United States Patent [19]
Tribou

[11] Patent Number: 5,852,258
[45] Date of Patent: Dec. 22, 1998

[54] GLOVE WEIGHING APPARATUS AND METHOD

[76] Inventor: Gene L. Tribou, 7728 Daetwyler Dr., Orlando, Fla. 32812

[21] Appl. No.: 944,630

[22] Filed: Oct. 6, 1997

[51] Int. Cl.$^6$ .................................................. G01G 19/00
[52] U.S. Cl. .................... 177/126; 177/148; 177/245; 177/253; 177/254; 2/905; 600/587; 341/20
[58] Field of Search ..................................... 177/245, 264, 177/126, 148, 149, 253, 254; 2/905; 600/587; 341/20

[56] References Cited

U.S. PATENT DOCUMENTS

| | | | |
|---|---|---|---|
| 626,052 | 5/1899 | Carter | 177/245 |
| 634,747 | 10/1899 | Crofford | 177/245 |
| 2,937,016 | 5/1960 | Westman | 265/67 |
| 3,090,454 | 5/1963 | Farrar et al. | 177/245 |
| 3,974,491 | 8/1976 | Sipe | 177/245 |
| 4,414,537 | 11/1983 | Grimes | 341/20 |
| 4,414,984 | 11/1983 | Zarudiansky | 600/587 |
| 4,870,868 | 10/1989 | Gastgeb et al. | 73/649 |
| 5,012,817 | 5/1991 | Zeilinski et al. | 600/587 |
| 5,429,140 | 7/1995 | Burdea et al. | 600/587 |
| 5,771,492 | 6/1998 | Cozza | 2/905 |

FOREIGN PATENT DOCUMENTS 54-0115165   9/1979   Japan ...................... 177/245

*Primary Examiner*—Randy W. Gibson
*Attorney, Agent, or Firm*—William M. Hobby, III

[57] ABSTRACT

A glove weighing apparatus includes a hand glove removably attachable to a person's hand which covers or has attached thereto a weighing device including a scale operatively attached to the weighing device. The scale is removably attached to a person's wrist or to the glove. The weighing device may be a pressure transducer, such as a piezoelectric crystal, which generates an electric signal responsive and analogous to the pressure applied thereto. The weighing device may also be a liquid filled container which applies a pressure to a diaphragm responsive to the weight placed on the weighing device. A weighing method includes attaching a weighing device to the palm side of a person's hand and attaching a hand glove over the person's hand and over the weighing device and then attaching a scale adjacent a person's hand and to the weighing device and placing material to be weighed in a person's hand and onto the attached weighing device to produce readings on the attached scale.

12 Claims, 1 Drawing Sheet

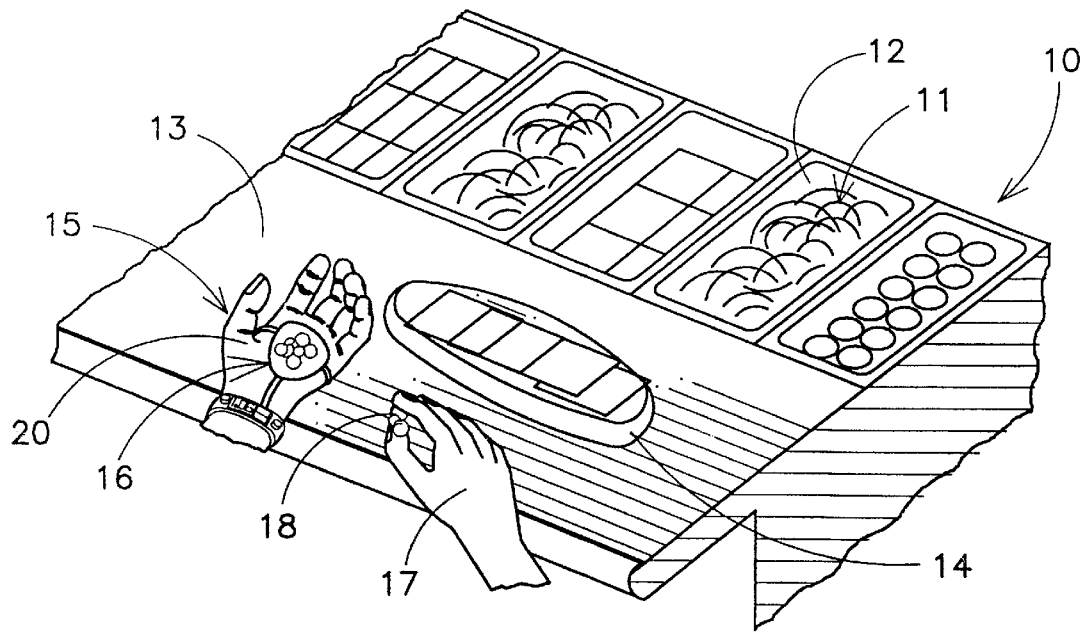
FIG. 1
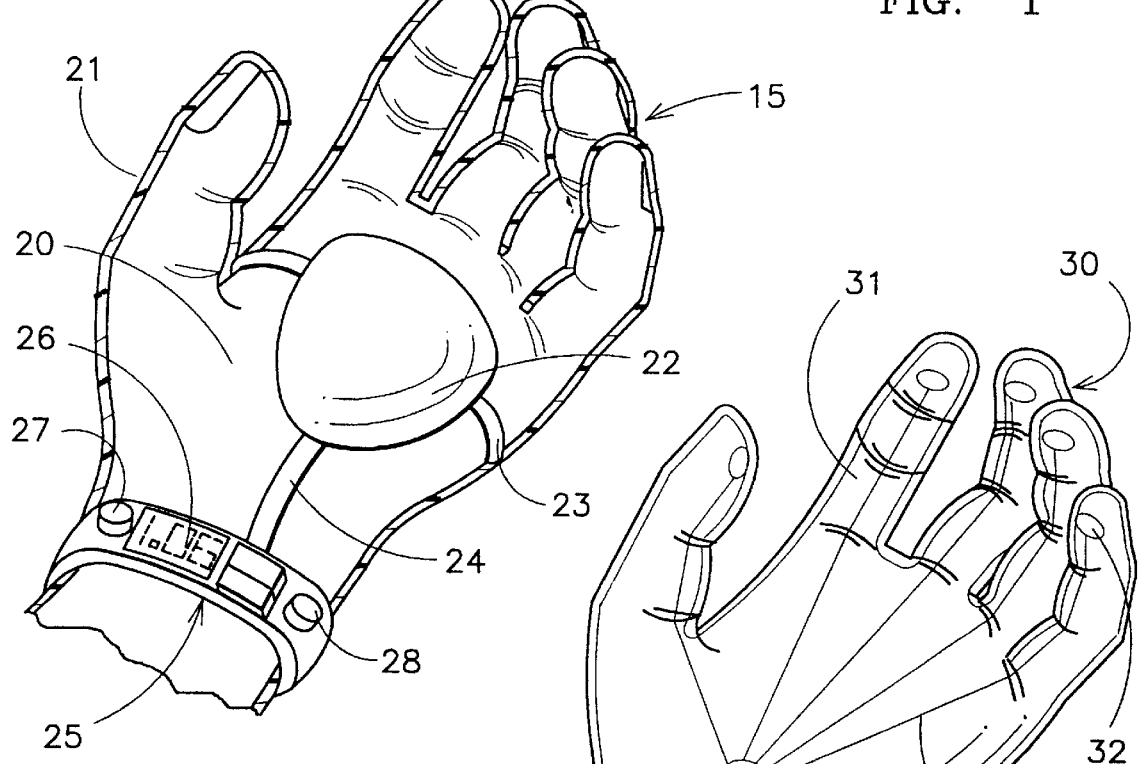
FIG. 2
FIG. 3

GLOVE WEIGHING APPARATUS AND METHOD

BACKGROUND OF THE INVENTION

The present invention relates to a hand attached weighing system and to a method of weighing materials supported in the palm of a person's hand.

In the past, it has been common to provide a wide variety of weighing scales for weighing different materials. Bathroom scales are used to determine a person's weight in their homes while retail stores use weighing scales for measuring various types of materials, such as food which is sold by weight. It is common to use small weighing scales in restaurants and food establishments especially to measure quantities of meat to provide uniform servings and for better cost control. Typically, scales for this purpose are placed adjacent where the meat or other food materials are being handled. The food materials are placed on the scale and small portions added or removed prior to placing on a food plate or sandwich.

The present invention is directed towards a weighing device for use in restaurants or other food establishments for the rapid determination of food or material quantity by weight and is provided with a glove weighing device in which the materials can be grasped in a glove covered hand and instantly weighed in the palm of the hand while reading a scale mounted on the glove or adjacent the hand.

Typical prior art U.S. patents for weighing devices may be seen in the Carter patent, U.S. Pat. No. 626,052 for ice weighing tongs in which a pair of ice tongs have incorporated a weighing device so that when the ice is grasped with the tongs and the weight rapidly ascertained. In the Crofford patent, U.S. Pat. No. 634,747, a combined scale and scoop is provided in which a person holding the scoop can scoop out food or other materials and determine the weight of the material scooped with the weighing scale. In the Westman patent, U.S. Pat. No. 2,937,016, and Farrar et al. patent, U.S. Pat. No. 3,090,454, handle weighing mechanisms are provided for luggage or bags so that by lifting the bag by the handle, provides the weight of the contents of the bag. There are a variety of other U.S. patents which combine the weighing of volume measurements with scoops or pouring devices. In contrast to these prior patents, the present invention provides for a glove incorporating a weighing device and having a scale formed thereon so that a person may slip on the glove combined with the weighing device, lift quantities of material in the palm of the hand, and obtain an instant reading from the scale. The present weighing device is especially adapted for use in restaurants and retail food establishments for obtaining a quick approximation of the weight of each portion of food being served.

SUMMARY OF THE INVENTION

A glove weighing apparatus includes a hand glove removably attachable to a person's hand which covers or has attached thereto a weighing device including a scale operatively attached to the weighing device. The scale is removably attached to a person's wrist or to the glove. The weighing device may be a pressure transducer, such as a piezoelectric crystal, which generates an electric signal responsive and analogous to the pressure applied thereto or a strain gage where the electrical resistance changes with applied strain. The weighing device may also be a liquid filled container which applies a pressure to a diaphragm responsive to the weight placed on the weighing device. A weighing method includes attaching a weighing device to the palm side of a person's hand and attaching a hand glove over the person's hand and over the weighing device and then attaching a scale adjacent a person's hand and to the weighing device and placing material to be weighed in a person's hand and onto the attached weighing device to produce readings on the attached scale.

BRIEF DESCRIPTION OF THE DRAWINGS

Other objects, features, and advantages of the present invention will be apparent from the written description and the drawings in which:

FIG. 1 is a partial perspective of a food service counter having the present weighing device on a person's hand;

FIG. 2 is a perspective view of a glove weighing apparatus in accordance with the present invention attached to a person's hand; and FIG. 3 is a perspective view of a second embodiment of a weighing glove in accordance with the present invention.

DESCRIPTION OF THE PREFERRED EMBODIMENT

Referring to the drawings and especially to FIG. 1, a food serving counter 10 has a variety of foods 11 in trays 12 adjacent a counter top 13. A serving plate 14 is positioned on the counter 13 and a person's left hand 15 has the weighing glove 16 thereon while the right hand 17 is placing portions of a food product on the palm 20 of the hand 16. The food portion is weighed prior to placing the portion on the serving platter 14.

In FIG. 2, the person's left hand 15 has a glove 21 mounted thereover and has a fluid filled flexible container 22 filled with a fluid, such as a liquid or gas, which has attaching straps 23 attaching the container 22 to the palm 20 of a person's hand 15. The flexible fluid filled container 22 has a passageway or tube 24 attached thereto and attached to a scale 25 which has been attached to a person's wrist. The scale 25 has the scale display 26 for displaying the weight. The tube 24 is attached to apply the fluid from the container 22 against a diaphragm which moves the scale responsive to the weight of the material placed on the container 22. Increasing the pressure of the fluid in the container by placing a mass thereon increases the fluid pressure in the tube 22. In FIG. 2, the scale 25 is shown converting the analog variations in the diaphragm to a digital readout 26. In addition, the apparatus has a scale adjustment knob 27 for zeroing the scale and an on/off knob 28.

In operation, the glove 21, which may have the weighing container 22 and the wrist scale 25 attached thereto is slid over the hand 15. Alternatively, the weighing attachment may be attached to the hand and a latex glove slid over the hand and over the weighing container, as illustrated in FIG. 2. The material to be weighed can then be picked up by the right hand 17, as illustrated in FIG. 1, and placed on the palm of the hand 15 until the approximate weight of a portion of food is determined at which time the food can be placed onto the platter 14 or onto a sandwich.

FIG. 3 illustrates a second embodiment in which the weighing apparatus is attached to a glove 30 which is attached to a person's hand 31. The scale 25 is also attached to the glove. The glove 30 has a microelectric pressure sensor 32 mounted at the tip of each finger which may be a pressure sensitive material, such as a piezoelectrical transducer which generates a voltage analogous to the amount of pressure applied thereagainst. Each pressure sensor 32 is connected through an electrical conductor 33 and through a central junction 34 to the scales 25 where the analog electrical signals are converted to a digital readout on the digital scale 26.

In the weighing scale of FIG. 3, a person slips the glove on and grasps and supports food with the fingers, such as a quantity of meat for a sandwich, while taking a readout on the digital scale 26 prior to placing the meat on the platter. The pressure applied to all of the pressure transducers 32 is summed to produce a composite signal which is analogous to the weight supported on the fingers.

It should be clear at this time that a glove weighing device has been provided which allows a person to fit a glove onto the hand for estimating the weight of materials, such as food products, in a rapid manner. The weighing method includes attaching the weighed device or glove having the weighing device therein to the person's hand with the scale attached on the glove adjacent the person's hand and then placing materials to be weighed in the weighing glove to produce a reading on the scale. A person can grasp and hold material to be weighed while reading the weight from the scale. However, the present invention should not be considered limited to the forms shown which are to be considered illustrative rather than restrictive.

I claim:

1. A glove weighing apparatus comprising:

weighing means for weighing a material, said weighing means being removably attachable to a the palm side of a person's hand;

a hand glove removably attachable over a person's hand and over said weighing means;

a scale operatively connected to said weighing means and removably attachable adjacent a person's hand whereby a person having said weighing means, glove and scale attached to a hand can determine the weight of material held in the hand.

2. A glove weighing apparatus in accordance with claim 1 in which said weighing means is attached to said glove whereby the weighing means and glove are removably attached to a person's hand together.

3. A glove weighing apparatus in accordance with claim 1 in which said weighing means includes a fluid filled container and having a passageway to said scale, whereby material supported on said fluid filled container applied a pressure to said scale.

4. A glove weighing apparatus in accordance with claim 1 in which said container is filled with a liquid.

5. A glove weighing apparatus in accordance with claim 1 in which said weighing means includes a plurality of pressure sensors.

6. A glove weighing apparatus in accordance with claim 5 in which each said pressure sensor is a piezoelectric pressure sensor.

7. A glove weighing apparatus in accordance with claim 1 in which said weighing means is attached in palm of a person's hand.

8. A glove weighing apparatus in accordance with claim 1 in which said weighing means is removably attached to a person's hand with a hook and loop fastener.

9. A glove weighing apparatus in accordance with claim 1 in which said scale is removably attached to a person's wrist with a hook and loop fastener.

10. A glove weighing apparatus in accordance with claim 5 in which each said sensor is attached to one of said fingers.

11. A glove weighing apparatus in accordance with claim 5 including a plurality of electrical conductors connecting said pressure sensor to said scale.

12. A weighing method comprising the steps of:

attaching a weighing means for weighing a material to the palm side of a person's hand;

attaching a hand glove over a person's hand and over said weighing means;

attaching a scale adjacent a person's hand and to said weighing means; and placing material to be weighted in a person's hand and onto the attached weighing means to produce a reading on the attached scale, whereby a person can grasp and hold a material to be weighed while reading the weight.

* * * * *